United States Patent [19]

Mazzocco

[11] Patent Number: 4,702,244
[45] Date of Patent: Oct. 27, 1987

[54] SURGICAL DEVICE FOR IMPLANTATION OF A DEFORMABLE INTRAOCULAR LENS

[75] Inventor: Thomas R. Mazzocco, Granada Hills, Calif.

[73] Assignee: Staar Surgical Company, Monrovia, Calif.

[21] Appl. No.: 834,200

[22] Filed: Feb. 27, 1986

Related U.S. Application Data

[62] Division of Ser. No. 346,105, Feb. 5, 1982, Pat. No. 4,573,998.

[51] Int. Cl.[4] .......................... A61B 17/00; A61F 2/16
[52] U.S. Cl. ...................................... 128/303 R; 623/6
[58] Field of Search ................ 623/6; 128/303 R, 321; 604/59, 60, 159

[56] References Cited

U.S. PATENT DOCUMENTS

| 2,761,446 | 9/1956 | Reed | 604/59 |
|---|---|---|---|
| 3,034,403 | 5/1962 | Neffe | 623/6 UX |
| 3,679,504 | 7/1972 | Wichterle . | |
| 3,703,174 | 11/1972 | Smith | 604/159 |
| 3,711,870 | 1/1973 | Dietrick | 623/6 |
| 3,757,781 | 9/1973 | Smart | 604/59 |
| 3,961,379 | 6/1976 | Highgate | 623/6 X |
| 3,991,426 | 11/1976 | Flom | 623/6 |
| 3,996,935 | 12/1976 | Banko | 128/276 |
| 4,002,169 | 1/1977 | Cupler, II | 128/276 |
| 4,053,953 | 10/1977 | Flom | 623/6 |
| 4,056,855 | 11/1977 | Kelman | 623/6 |
| 4,080,709 | 3/1978 | Poler | 29/412 |
| 4,092,743 | 6/1978 | Kelman | 623/6 |
| 4,110,848 | 9/1978 | Jensen | 623/6 |
| 4,118,808 | 10/1978 | Poler | 623/6 |
| 4,122,556 | 10/1978 | Poler | 623/6 |
| 4,139,513 | 2/1979 | Tanaka . | |
| 4,139,692 | 3/1979 | Tanaka . | |
| 4,153,641 | 5/1979 | Deichert . | |
| 4,172,297 | 10/1979 | Schelegel | 623/6 |
| 4,206,518 | 6/1980 | Jardon | 623/6 |
| 4,214,585 | 7/1980 | Bailey, Jr. | 128/303 R |
| 4,251,887 | 2/1981 | Anis | 623/6 |
| 4,253,199 | 3/1981 | Banko | 623/6 |
| 4,254,509 | 3/1981 | Tennant | 623/6 |
| 4,261,875 | 4/1981 | Le Boeuf . | |
| 4,262,370 | 4/1981 | Hartstein | 623/6 |
| 4,285,073 | 8/1981 | Szycher | 623/6 |
| 4,373,218 | 2/1983 | Schachar | 623/6 |

Primary Examiner—Ronald L. Frinks
Attorney, Agent, or Firm—Frank Frisenda, Jr.

[57] ABSTRACT

The invention provides an improved intraocular lens structure comprising a deformable optical zone portion with prescribed memory characteristics and methods and devices for implantation of such lens in the eye. The unique optical zone portion of the lens can be deformed by compressing, rolling, folding, stretching, or can be deformed by a combination of these techniques to temporarily reduce the optical zone portion to a diameter of about 80% or less of the cross-sectional diameter of the optical zone portion in an unstressed state. After insertion into the eye, the optical zone portion returns to its original configuration, full size and fixed focal length. The inventive methods and devices for implantation permit insertion of the improved lens through a relatively small incision made in the ocular tissue, thereby providing a safer, more convenient surgical procedure and more comfortable fit for the eye.

12 Claims, 63 Drawing Figures

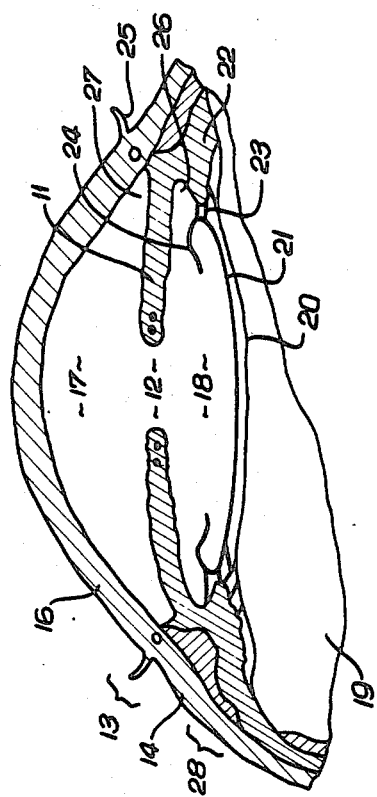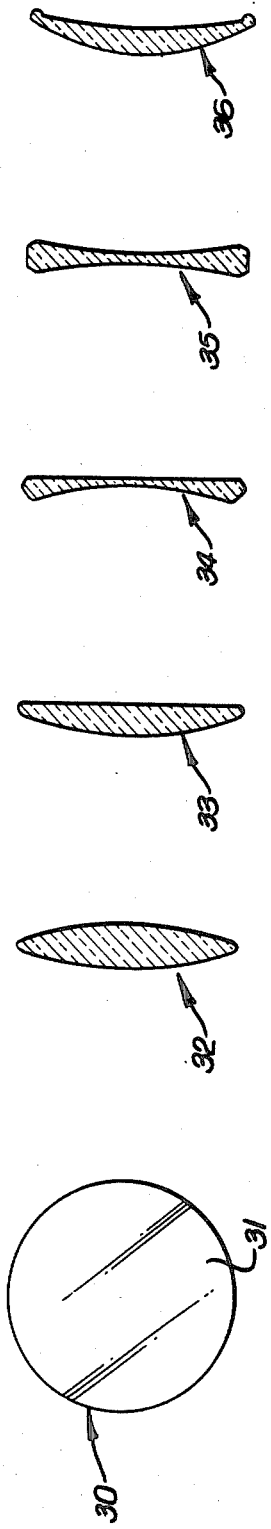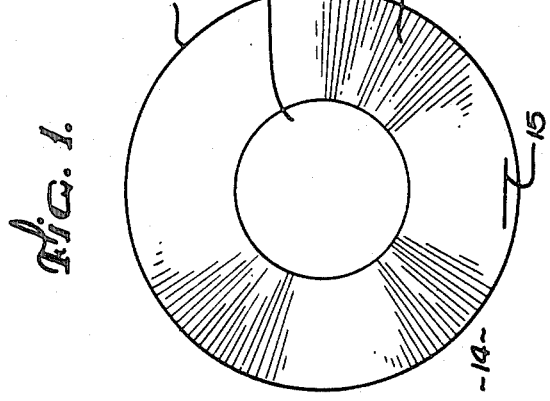

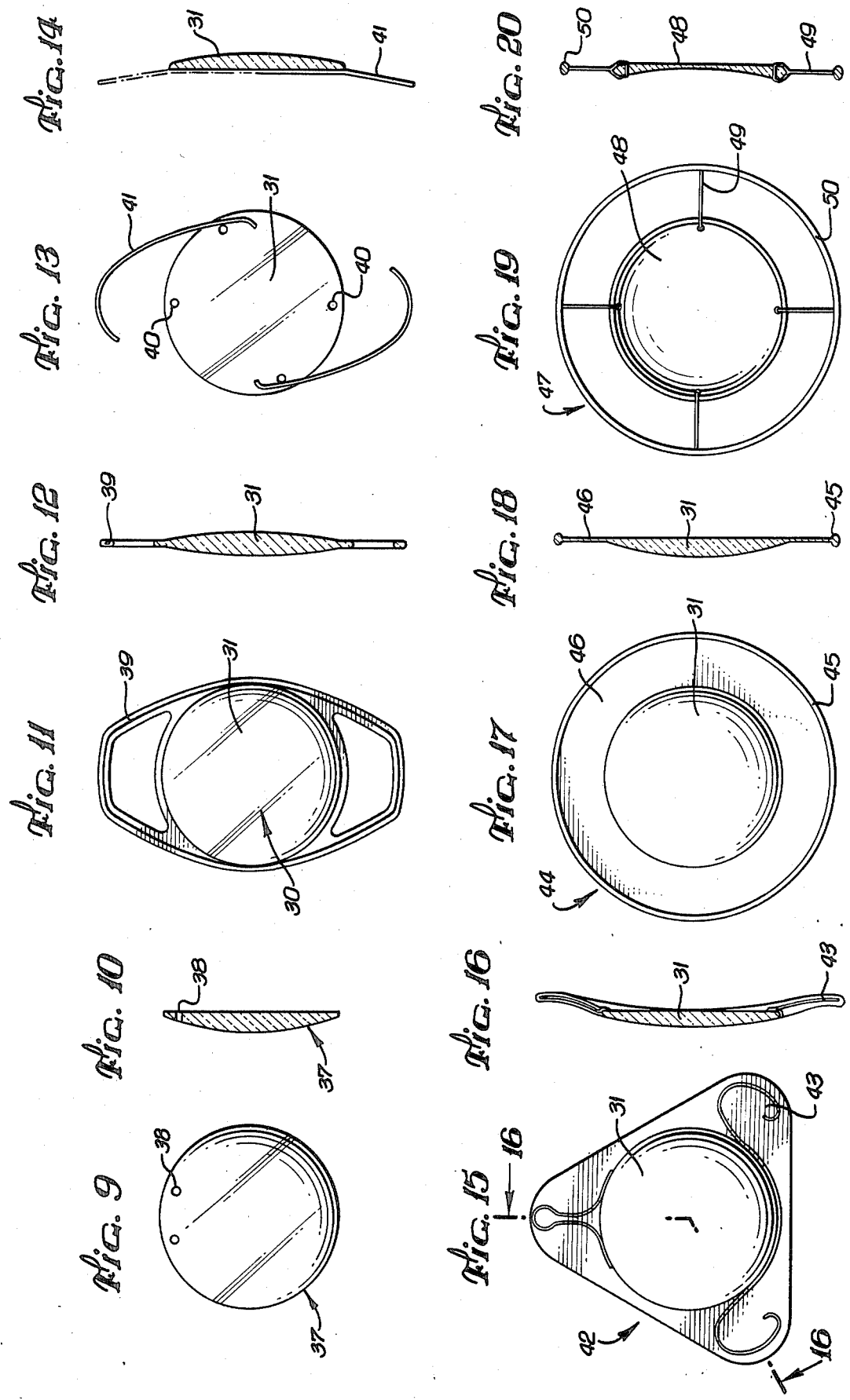

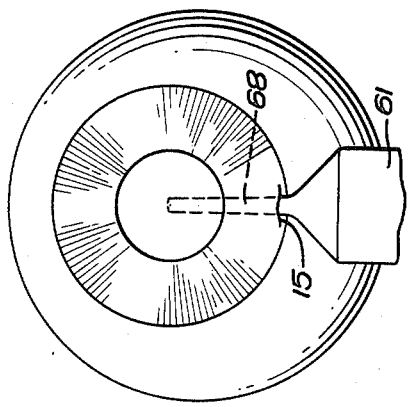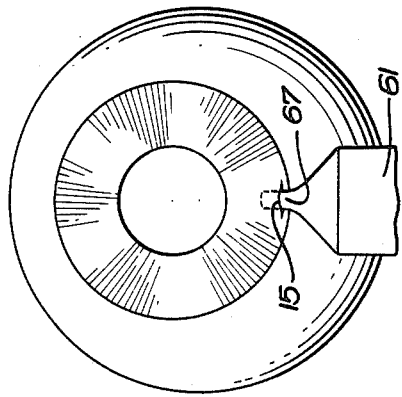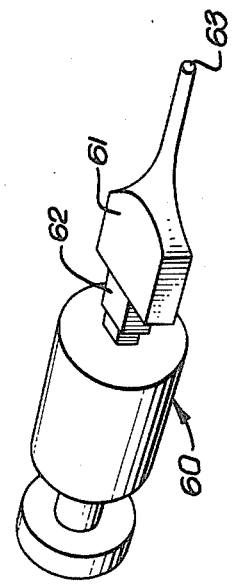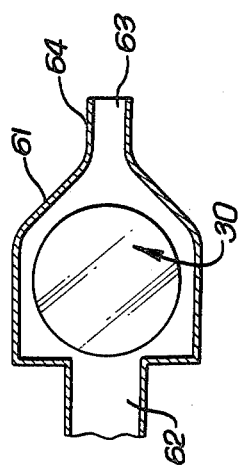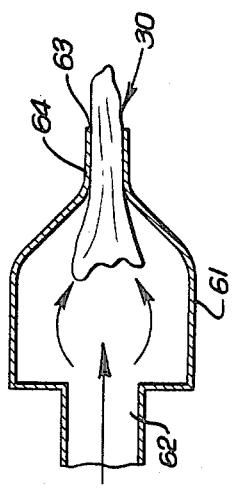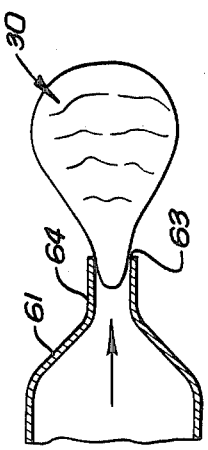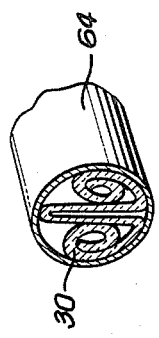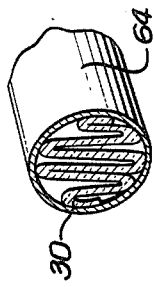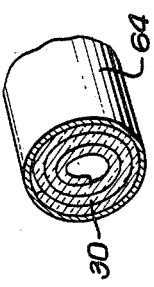

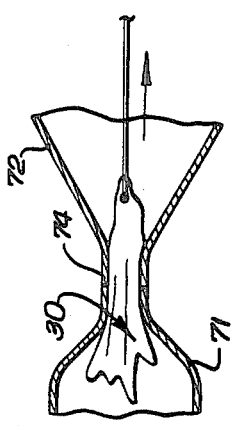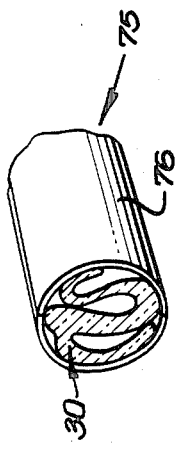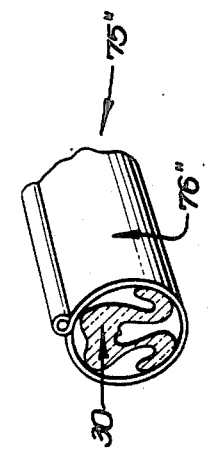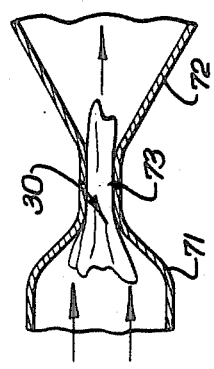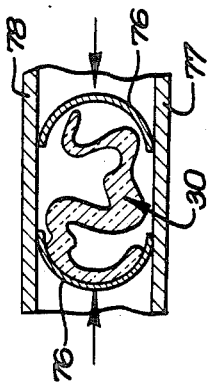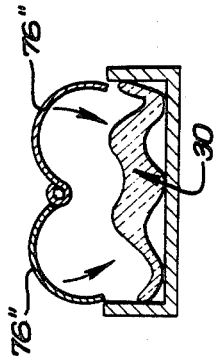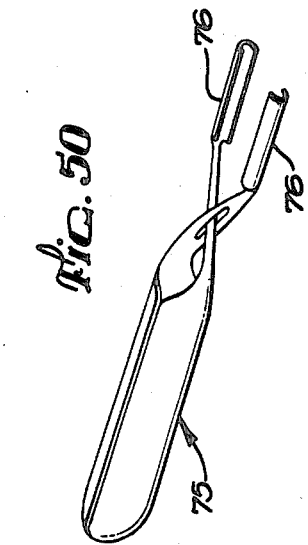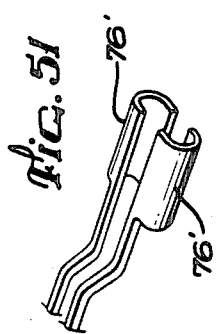

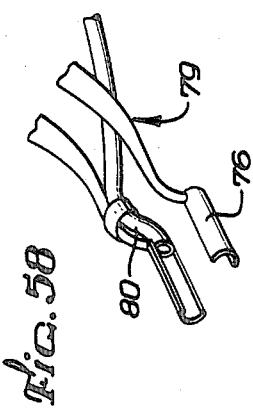
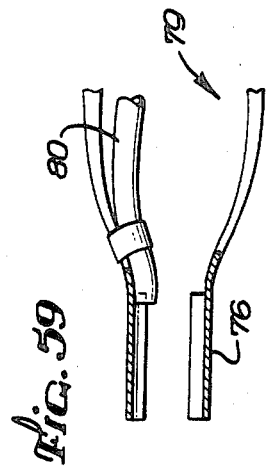
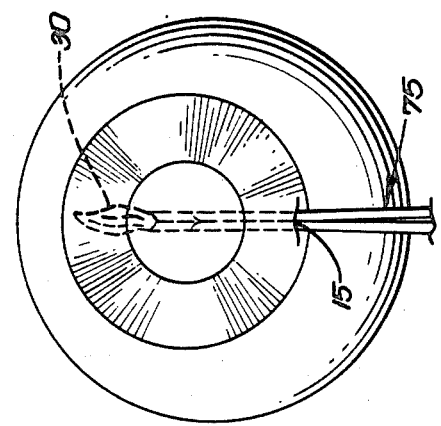
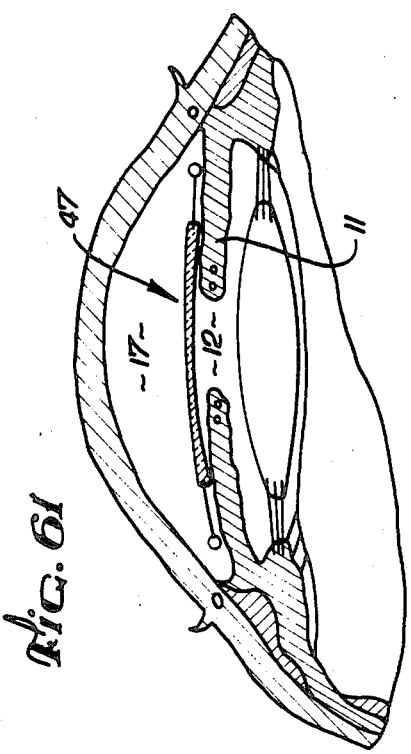
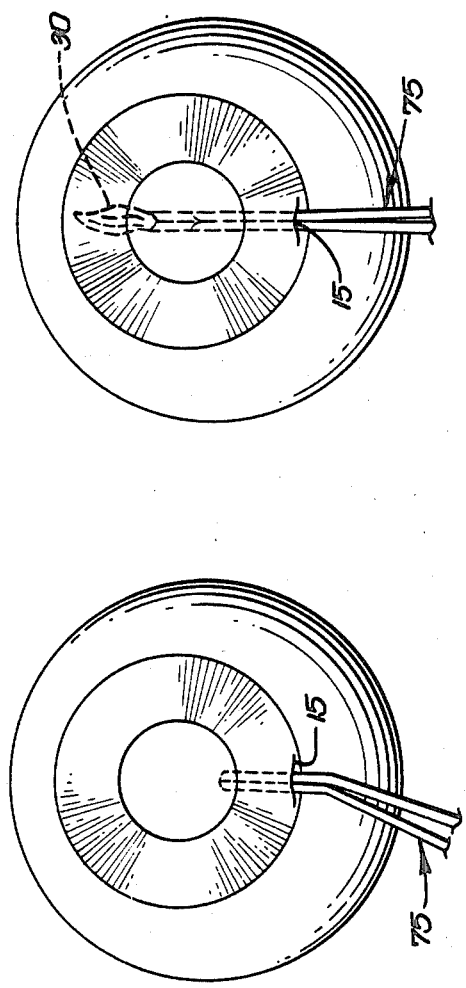
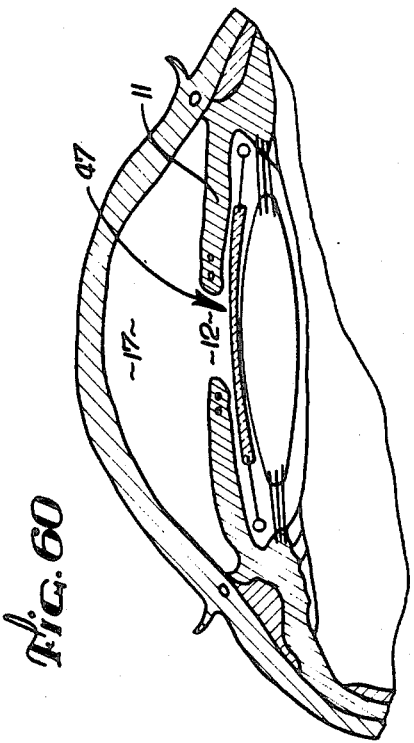

SURGICAL DEVICE FOR IMPLANTATION OF A DEFORMABLE INTRAOCULAR LENS

This is a divisional of application Ser. No. 346,105 filed Feb. 5, 1982, now U.S. Pat. No. 4,573,998.

BACKGROUND OF THE INVENTION

Intraocular lenses have gained wide acceptance in replacement of human crystalline lens after a variety of cataract removal procedures. The human crystalline lens is generally recognized to be a transparent structure having a thickness of about 5 millimeters and diameter of about 9 millimeters. The lens is suspended behind the iris by zonular fibers which connect the lens to the ciliary body. A lens capsule surrounds the lens, the front portion of the capsule being commonly known as the anterior capsule and the back portion commonly known as the posterior capsule.

Numerous procedures for the removal of cataracts have been developed in which the lens is removed from the eye and replaced by an artificial lens implant. The extraction procedure may be generally categorized as intracapsular (in which the lens is removed together with the lens capsule) or extracapsular (in which the anterior capsule is removed with the lens, and the posterior capsule is left intact).

Since Ridley implanted the first artificial lens in about 1949, the problems associated with cataract extraction and lens implantation have received a great deal of attention from ophthalmic surgeons.

Various types of artificial lenses have been proposed, and appropriate surgical procedures have been developed which strive to reduce patient discomfort and reduce post-operative complications. Reference is made in this connection to *Pseudophakos* by N. Jaffe, et al; "History of Intraocular Implants" by D. P. Choyce (Annals of Opthalmology, Oct. 1973); U.S. Pat. No. 3,991,426 issued to Flom on Nov. 16, 1976; and U.S. Pat. No. 4,092,743 issued to Kelman on Nov. 8, 1977 which disclosures are hereby incorporated by this reference.

Of particular interest in the context of the present invention is the development of surgical techniques requiring relatively small incisions in the ocular tissue for the removal of cataracts as disclosed in U.S. Pat. No. 4,002,169 and U.S. Pat. No. 3,996,935. A number of skilled artisans have disclosed intraocular lens structures comprising an optical zone portion generally made of rigid materials such as glass or plastics suitable for optical use.

However, one of the principle disadvantages of the conventional rigid intraocular lens is that implantation of the lens requires a relatively large incision in the ocular tissue. This type of surgical procedure leads to a relatively high complication rate, among other disadvantages. For instance, the serious dangers associated with implantation of a rigid lens structure include increased risks of infection, retinal detachment, and laceration of the ocular tissues, particularly with respect to the pupil.

Accordingly, those skilled in the art have recognized a significant need for an intraocular lens implant which affords the clinical advantages of using relatively small incision techniques, yet possesses an optical zone portion having a fixed focal length and which will retain a prescribed configuration once, implanted in the central optical area, thereby providing a safer and more convenient surgical procedure and comfortable fit for the eye. The present invention fulfills these needs.

SUMMARY OF THE INVENTION

This invention relates to an improved intraocular lens structures, methods and instrumentation for implantation of the lens through a relatively small incision made in the ocular tissue. In more detail, the inventive lens structures comprise a deformable optical zone portion having a prescribed memory characteristics which enable the lens to be deformed by compressing, rolling, folding, stretching, or by a combination thereof, to a diameter of 80% or less of the cross-sectional diameter of the optic, and yet return to its original configuration, full size and fixed focal length after insertion in the eye. The unique optical zone portion can be fabricated from selected biologically inert materials possessing superior elasticity and compression characteristics and optionally, may include a wide variety of support appendages.

The embodied methods for implantation of the artificial intraocular lens can be utilized for replacement of, or for refractive correction of, a human crystalline lens. These inventive methods include:

providing an intraocular lens having a deformable optical zone portion with prescribed memory characteristics; deforming the optical zone portion of the lens to a diameter of about 80% or less of the cross-sectional diameter of the optic in an unstressed state; inserting the intraocular lens through a relatively small incision made in the ocular tissue; allowing the lens implant to return to its original configuration, full size and fixed focal length after insertion in the eye; whereby a safer, more convenient surgical procedure and more comfortable fit for the eye is achieved.

Further, the present invention provides unique instrumentation for deforming and inserting the lens through a small incision during implantation. In one embodied form, the instrumentation comprises a single micro-hook type device adapted to fit the lens to enable the lens to be appropriately deformed and pulled through the incision made in the ocular tissue. In a second embodied form, a double micro-hook type device is provided which enables the lens to be stretched in a direction perpendicular to the incision in an amount sufficient to allow insertion of the lens through a relatively small incision made in the ocular tissue. In yet a third embodied form, the instrumentation comprises an injection type device especially adapted to compress the inventive lens through a cannula and insert the lens into the eye. In a fourth embodiment, the instrumentation comprises a forceps type device having a compressor member to partially or fully encase and deform the intraocular lens to facilitate insertion within the eye.

Thus, the present invention offers a unique implantation system for correction of or replacement of a human crystalline lens after, for instance, cataract removal by way of small incision technique.

The above and other objects and advantages will become apparent from the following more detailed description of the invention, taken in conjunction with the drawings.

BRIEF DESCRIPTION OF THE DRAWINGS

FIG. 1 is a stylized frontal view of a human eye illustrating a relatively small surgical incision made in the ocular tissue relative to major eye components for purposes of referencing the description of deformable intraocular lens implants in accordance with the present invention;

FIG. 2 is a partially side sectional view of the human eye shown in FIG. 1 illustrating the internal condition of the ocular area after extracapsular cataract extraction in accordance with conventional procedure;

FIG. 3 is a front elevational view of one embodied form of a deformable intraocular lens in accordance with the present invention;

FIG. 4 is a side sectional view of the intraocular lens shown in FIG. 1 of a biconvex lens specie;

FIG. 6 is a side sectional view of the intraocular lens shown in FIG. 1 of a plano convex lens specie;

FIG. 6 is a side sectional view of the intraocular lens shown in FIG. 1 of a plano concave lens specie;

FIG. 7 is a side sectional view of the intraocular lens shown in FIG. 1 of a biconcave lens specie;

FIG. 8 is a side sectional view of the intraocular lens shown in FIG. 1 of a concave-convex lens specie;

FIG. 9 is a front elevational view of a second embodied intraocular lens including means for facilitating suturing, manipulation, or fluid flow;

FIG. 10 is a side sectional view of the intraocular lens shown in FIG. 9; indicating holes perforating the full thickness of the lens;

FIG. 11 is a front elevational view of a third embodied intraocular lens provided with fixating appendages having optional compressible internal support elements;

FIG. 12 is a side sectional view of the intraocular lens shown in FIG. 11 illustrating uniplanar fixating appendages;

FIG. 13 is a front elevational view of fourth embodied intraocular lens including means for facilitating suturing, manipulation, or fluid flow and comprising non-integral fixating appendages;

FIG. 14 is a side sectional view of the intraocular lens shown in FIG. 13, this embodiment, illustrating the fixating appendages as angulated;

FIG. 15 is a front elevational view of a fifth embodied intraocular lens having angulated compressible fixating appendages with internal supporting elements;

FIG. 16 is a side sectional view of the intraocular lens shown in FIG. 15;

FIG. 17 is a front elevational view of a sixth embodied intraocular lens having a compressible peripheral support ring and illustrating a tinted or occluded periphery;

FIG. 18 is a side view of the intraocular lens shown in FIG. 17;

FIG. 19 is a front elevational view of a seventh embodied intraocular lens, the optical portion of the lens being suspended by threads or spokes from a non-integral peripheral support ring;

FIG. 20 is a side sectional view of the intraocular lens depicted in FIG. 19;

FIG. 22a is a side sectional view of the fixated intraocular lens depicted in FIG. 21a;

FIG. 37 is a perspective view of a fourth embodied device of the injection type utilized to compress the deformable intraocular lens during insertion into the eye;

FIG. 38 is an enlarged fragmentary view of the forward portion of the insertion device shown in FIG. 37 and further illustrating a transparent lens holding chamber of the device, the lens being in a natural unstressed state;

FIG. 39 is an enlarged fragmentary view of the forwardly mounted lens holding chamber of the device depicted in FIG. 37 and illustrates the lens undergoing deformation and expulsion from the device by action of fluid pressure exerted on a rear section of the lens;

FIG. 40 is an enlarged fragmentary view of the tip of the lens holding chamber of the device of FIG. 37 illustrating the deformable intraocular lens returning to its original unstressed shape as it exists from the mouth of the extension cannula for implantation in the eye;

FIG. 41 is a front sectional view of an embodied implant procedure wherein the device of FIG. 37 is fitted with a short nozzle at the forward portion of the lens holding chamber for releasing the lens just through the incision for anterior chamber or posterior chamber fixation;

FIG. 42 is a front sectional view of an implant procedure utilizing the device shown in FIG. 37, the lens holding chamber having an extension cannula utilized to facilitate placement of the lens in the posterior chamber through the pupil;

FIG. 43 is a longitudinal perspective view of the nozzle portion of the lens holding chamber depicted in FIG. 37 illustrating the lens in a rolled condition as it undergoes deformation during the implant procedure;

FIG. 44 is a longitudinal perspective view of the nozzle portion of the lens holding chamber depicted in FIG. 37 illustrating the lens in a folded condition;

FIG. 45 is a longitudinal perspective view of the nozzle portion of the lens holding chamber depicted in FIG. 37 illustrating the lens in a partly rolled and partly folded condition;

FIG. 46 is a longitudinal perspective view of the nozzle portion of the lens holding chamber depicted in FIG. 37 illustrating the lens in a random "crumple" fold condition;

FIG. 47 is a perspective view of yet another embodied device of the injection type utilized for implantation of the inventive intraocular lens in accordance with the present invention illustrating a lens holding compartment mounted beyond the orifice of the device;

FIG. 48 is an enlarged fragmentary view in section of the joinder between the lens holding compartment and orifice of the device depicted in FIG. 47 undergoing extraction of the lens from the compartment by means of suction exerted from the cannula and loading the device for entry into the ocular incision;

FIG. 49 is an enlarged fragmentary view of the joinder between the lens holding compartment and orifice of the device depicted in FIG. 47 and illustrates an alternate method of loading the cannula of the device by means for pulling the lens from the compartment to the orifice;

FIG. 50 is a top view of yet another embodied implantation instrument of the forceps type utilzed to deform the intraocular lens during insertion through the ocular incision;

FIG. 51 is a fragmentary view of the instrument depicted in FIG. 50 having modified ends to deform the lens with a minimum amount of pressure exerted by the instrument on the lens in the maximum cross-sectional volume present in the ocular incision;

FIG. 52 is a schematic cross-sectional view of the instrument depicted in FIG. 50 illustrating the device in a partially closed state with the intraocular lens being partly deformed; two rigid plates are shown to hold the lens in the plane of the forceps to facilitate enclosure;

FIG. 53 is a longitudinal cross-sectional view of the inventive forceps type instrument fully deforming an intraocular lens therein;

FIG. 54 is a longitudinal sectional view of the forward end of the inventive forceps type device having a hinged compressing mechanism and a rigid bowl-shaped accessory to facilitate lens encasement and release performance of the device within the eye;

FIG. 55 is a cross-sectional view of the device illustrated in FIG. 54, the intraocular lens being completely encased within the hinged compressing mechanism;

FIG. 56 is a front sectional view of an implant procedure utilizing the forceps type device shown in FIG. 50 to place the intraocular lens in a posterior chamber through a relatively small incision and iridectomy;

FIG. 57 is a front sectional view of an implant procedure utilizing a "cut away" forceps type device to place the intraocular lens in a posterior chamber through the pupil;

FIG. 58 is an enlarged fragmentary sectional view of the forward end of a forceps type device including a modification designed to use hydraulic pressure to eject the lens out of the forcep ends and into the eye similar to the procedure shown in FIGS. 39 and 40 above;

FIG. 59 is a top view of the device depicted in FIG. 58;

FIG. 60 is a side sectional view of an eye with natural crystalline lens intact and an intraocular lens of the corrective type as shown in FIG. 20 in position in the posterior chamber between the iris and human crystalline lens;

FIG. 61 is a cross-sectional view of an eye with human crystalline lens intact and an intraocular lens in position in the anterior chamber of the eye for corrective purposes.

DESCRIPTION OF THE PREFERRED EMBODIMENTS

Figure 21A:
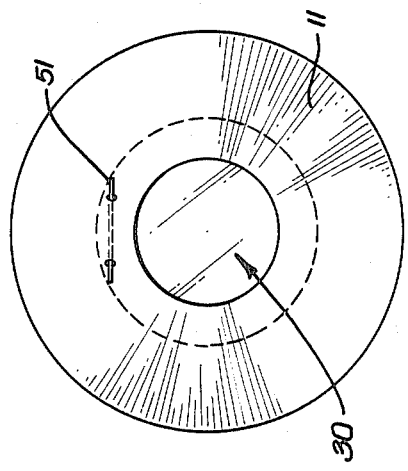
FIG. 21a is a front view illustrating the intraocular lens of FIG. 3 fixated to the iris of the eye in back of the pupil.

The present invention provides deformable intraocular lens structures having prescribed memory characteristics and methods and instrumentation for implantation of such lens for correction of or replacement of a human crystalline lens. A unique optical zone portion of the intraocular lens possesses memory characteristics such that the lens can be deformed by compressing, rolling, folding or stretching the optical zone portion to a diameter of 80% or less than the cross-sectional diameter of the optic during insertion into the eye yet return to its original configuration, size and fixed focal length once implanted in the eye, thereby providing a safer, more convenient, and more comfortable surgical procedure.

Referring now to the drawing, denoted FIG. 1, there is shown a stylized frontal view of an eye illustrating the major ocular components: iris 11, pupil 12, limbus 13, sclera 14 relative to a small incision 15 made in the ocular tissue, for instance, implantation of an intraocular lens in accordance with the present invention.

FIG. 2 represents a side cross-sectional view of the eye shown in FIG. 1 and illustrates major ocular components in more detail. The cornea 16 is composed of clear tissue which connects to the sclera 14 at the limbus 13. The anterior segment of the eye is divided into two principle chambers by the iris 11 and pupil 12. An anterior chamber 17 is defined by the space between the cornea 16 and the iris 11. A posterior chamber 18 is defined by the space between the iris 11 and the vitreous 19.

In surgical procedures commonly known as intracapsular cataract extraction, the posterior chamber 18 is bounded by the hyloid membrane 20. In surgical procedures commonly known as the extracapsular cataract extraction, the posterior chamber 18 is bounded by the posterior capsule 21 attached to the ciliary body 22 by means of zonular fibers 23. Portions of the anterior capsule may remain as flaps 24, creating, with the posterior capsule, 21 the ocular portion commonly known as the "capsular bag". The posterior chamber 18 peripheral area between the iris 11 and the extension of the ciliary body 22 is referred to as the cilary sulcus 26. The anterior chamber peripheral area between the cornea 16 and the iris 11 is referred to as the angle 27 of the eye. The area of the clear posterior to the plane of the iris and anterior to the vitreous 19 is known as pars plana 28.

With the foregoing referenced ocular components in mind, it is a principle feature of the present invention to provide a class of intraocular lens structures having a deformable optical zone portion such that the lens with optional fixation appendages can be deformed by compressing, rolling, folding or stretching to a diameter of 80% or less of the cross-sectional diameter of the optic during insertion into the eye, yet return to its original full size and fixed focal length once implanted in the eye. Accordingly, the inventive intraocular lens structures can be implanted through smaller incisions made in the ocular tissue than would be possible with any rigid intraocular lens of comparable size.

FIG. 3 depicts an intraocular lens 30 in accordance with the present invention which is suitable for use as an artificial lens implant. In the embodied form shown, there are no fixation appendages and the lens comprises a deformable optical zone portion 31 imparted with desirable memory characteristics, appropriate structural dimensions, and composed of a deformable material such that the lens can be deformed to an appropriate size for insertion into the eye.

Typically, the optical zone portion 31 of the lens 30 is composed of one or more suitable materials such as polyurethane elastomer, silicone elastomer, hydrogel polymer collagen compounds, organic or synthetic gel compounds and combinations thereof. In one embodied form, the optical zone portion 31 of the lens can be fabricated having a base member composed of any of the foregoing materials, and further comprise a surface layer or layers of a second or third material. Moreover, the lens may be tinted, colored or fabricated with occluded portions to yield desired transmission effects.

As shown in FIGS. 4, 5, 6, 7, and 8, the inventive lens can be fabricated having a wide variety of cross-sections designed for replacement of the surgically removed human crystalline lens or for refractive correction without removal of the human crystalline lens. In this respect, the FIGS. 4-8 illustrate respectively a convex lens 32, a plano convex lens 33, a plano concave lens 34, a biconcave lens 35, and a concave-convex lens 36.

Referring to FIG. 9, there is illustrated another embodied intraocular lens structure 37 in accordance with the present invention, the lens being provided with means 38 for assisting suturing, manipulation, or fluid flow through the lens. In this respect, the lens may optionally be provided with one or more holes 38, suitably located, which may extend entirely through the cross-section of the lens as shown in FIG. 10, or partially through the cross-section of the lens as an indentation for facilitating meneuvering of the lens during surgical procedues.

Further, in accordance with the present invention, the inventive intraocular lens structures may comprise integral or nonintegral appendages to facilitate positioning of the lens within the eye. FIGS. 11-20 illustrate a wide variety of appendages which may be utilized.

In more detail, FIG. 11 depicts an intraocular lens 30 optionally provided with appendages 39 of the compressible-integral support element type. As seen in FIG. 12, the appendages 39 in this embodiment are uniplanar with the optical zone portion 31 of the lens.

FIGS. 13 and 14 depict the inventive intraocular lens provided with a plurality of holes 40 therethrough and angulated support appendages 41 with respect to the plane of the optic. Such appendages may be composed of any suitable material and may be selected from a material different from that of the optical zone portion of the lens.

FIGS. 15 and 16 illustrate an inventive intraocular lens 42 provided with angulated compressible appendages 43 with internal supporting elements. That is, the supporting structure is internally contained within the appendages as shown.

FIGS. 17 and 18 depict an inventive intraocular lens 44 having a deformable peripheral support ring 45 and a tinted or occluded periphery 46 which is a substantially continuous peripheral flange.

FIGS. 19 and 20 illustrate yet another intraocular lens structure 47 in accordance with the present invention wherein the optical zone portion 48 is suspended by threads or spokes 49 from a peripheral supporting ring 50 constructed of a suitable material.

As will readily be appreciated by those skilled in the art, the foregoing specific embodiments are merely illustrative of the wide variety of intraocular lens structures included within the spirit and scope of this invention. In this respect, it should be understood that the provision of appendages and means for facilitating manipulation, fixation or fluid flow thorugh the lens are optional. The latter means includes holes, openings, depressions and/or passageways to aid the surgical procedure.

Figure 22A:
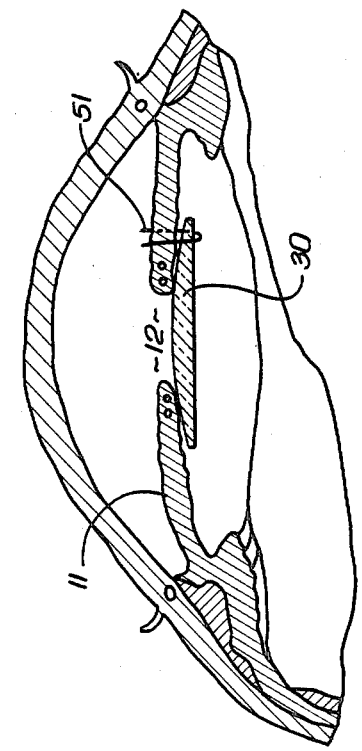
Figure 21:
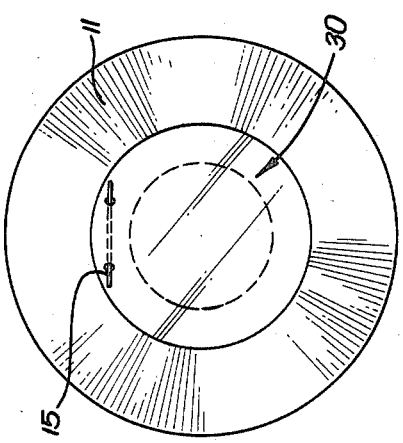
FIG. 21 is a front view illustrating the intraocular lens depicted in FIG. 3 fixated to the iris of the eye in front of the pupil.
Figure 22:
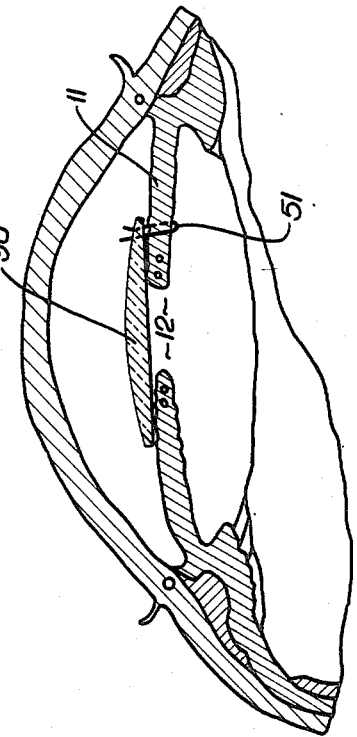
FIG. 22 is a side sectional view of the intraocular lens depicted in FIG. 21.

FIGS. 21 and 22 illustrate implantation of the intraocular lens 30 fixated to the iris 11 of the eye in front of the pupil 12. In the depicted embodiment, a piercing suture 51, such as one fabricated from stainless steel, is disposed at an appropriate location along the lens periphery and inserted through the iris 11 in a surgical procedure which replaces the human crystalline lens previously extracted from the eye. While the foregoing figures illustrate fixation of the lens 30 shown in FIG. 3, it should be readily understood that each of the foregoing embodied lens structures could be also fixated in a similar manner.

FIGS. 21a and 22a illustrate an alternative positioning of the intraocular lens 30 in accordance with the present invention, behind the iris 11 of the eye, behind the pupil 12. In the illustrated embodiment, the lens 30 is also sutured in place by means of a piercing suture 51 such as one composed of stainless steel.

Figure 23:
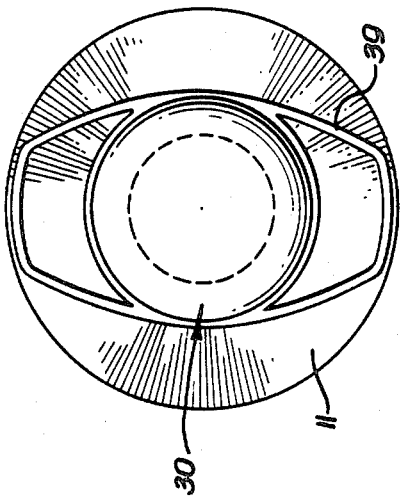
FIG. 23 is a front view of the intraocular lens shown in FIG. 11 fixated in the anterior chamber of the eye in front of the iris, the lens having uniplanar, integral support appendages to position the optic over the pupil.
Figure 24:
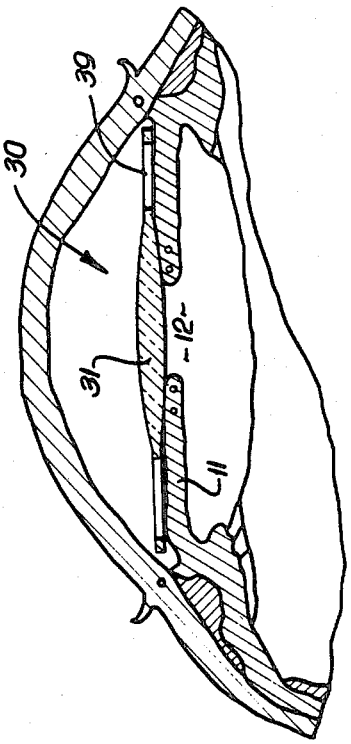
FIG. 24 is a side sectional view of the fixated lens as shown in FIG. 23.

FIGS. 23 and 24 depicts a typical positioning of the intraocular lens 30 shown in FIGS. 11 and 12 in the anterior chamber of the eye in front of the iris 11, with supporting appendages 39, to fixate the optic over the pupil 12. In these illustrations the lens is shown without the optional internal supporting elements.

Figure 25:
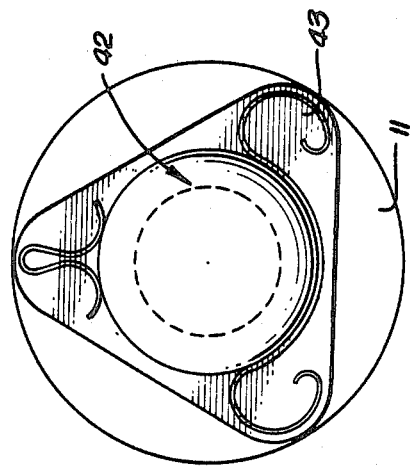
FIG. 25 is a front view of the lens shown in FIG. 15 fixated in a position in front of the iris and pupil.
Figure 26:
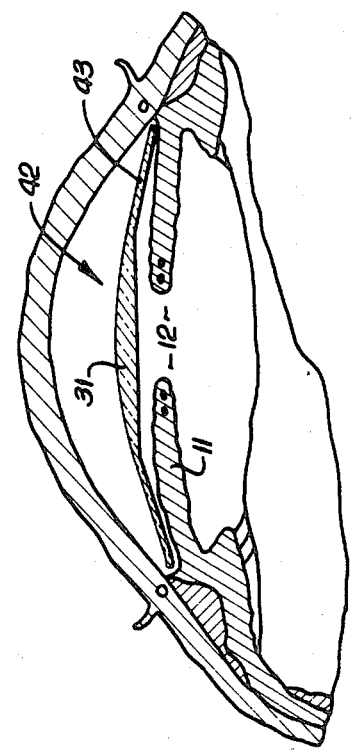
FIG. 26 is a side sectional view of the fixated lens as shown in FIG. 25.

FIGS. 25 and 26 illustrate positioning of the intraocular lens 42 shown in FIGS. 15 and 16 in a position in front of the iris 11 and the pupil 12 with supporting appendages 43 angulated with respect to the plane of the optic.

Figure 27:
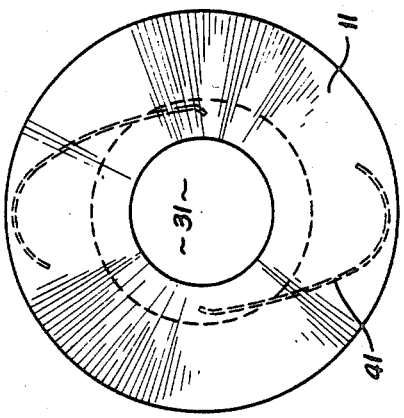
FIG. 27 is a front view of the intraocular lens depicted in FIG. 13 illustrating fixation of the lens behind the iris and pupil.
Figure 28:
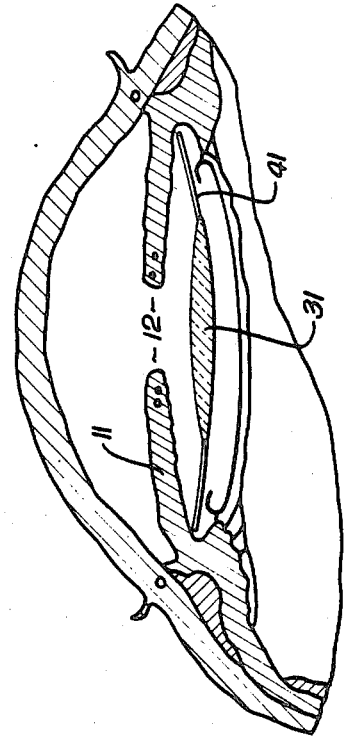
FIG. 28 is a side view of the fixated lens shown in FIG. 27 illustrating positioning of support appendages in front of the ciliary body and the lens optic in front of the posterior capsule.

FIGS. 27 and 28 illustrate placement of the intraocular lens shown in FIGS. 13 and 14 in a position behind the iris 11 and pupil 12. The supporting appendages 41 are positioned in front of the ciliary body 22 and the optical zone portion of the lens is positioned in front of the posterior capsule 21.

Figure 29:
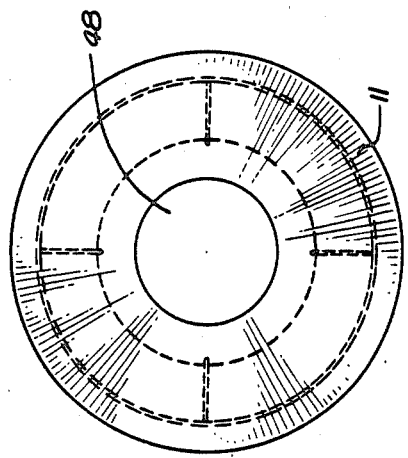
FIG. 29 is a front view illustrating the lens depicted in FIG. 19 fixated behind the iris and pupil.
Figure 30:
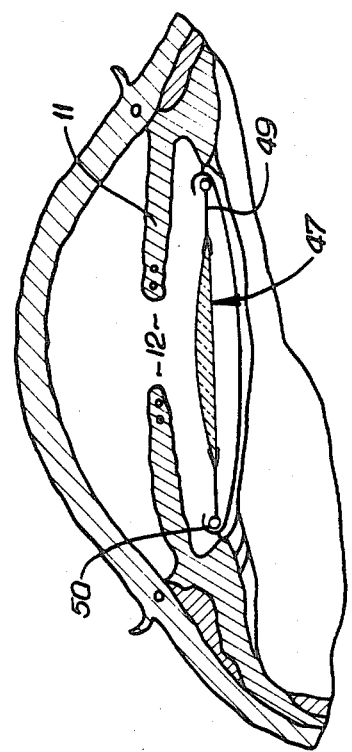
FIG. 30 is a side sectional view of the fixated lens shown in FIG. 29 further illustrating the lens in position within the capsular bag.

FIGS. 29 and 30 depict the intraocular lens 47 shwon in FIGS. 19 and 20 after implantation, and positioned behind the iris 11 and the pupil 12 within the capsular bag.

Accordingly, those skilled in the art will readily appreciate that the deformable intraocular lens implant provided by the present invention can be fixated in the eye in a wide variety of locations and that a wide variety of supporting appendages may optionally be included with the deformable optical zone portion of the lens to fixate the lens in the desired position.

One important feature of the lens in accordance with the present invention is that it lends itself to positions which allow the free mobility of the pupil, that is, in terms of normal pupillary functions when in place in the eye.

The present invention further provides unique methods and devices for implantation of the intraocular lens by temporarily deforming the optical zone portion to a diameter of 80% or less of the cross-sectional diameter of the optical zone portion in an unstressed state. After insertion into the eye, the optical zone portion returns to its prescribed original optical configuration, full size, and fixed focal length, thereby providing a safer, more convenient surgical procedure and more comfortable fit for the eye.

Figure 32:
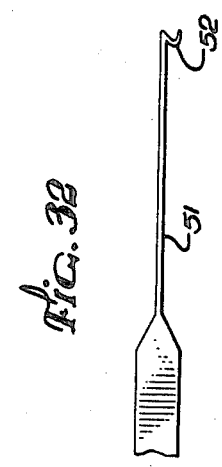
FIG. 32 is a side sectional view of the microhook type instrument utilized in the insertion technique shown in FIG. 31.
Figure 31:
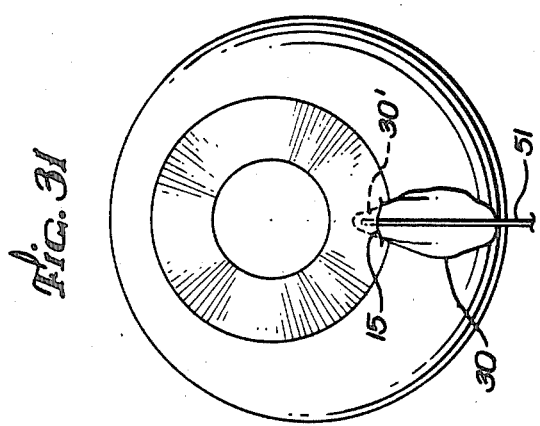
FIG. 31 is a partial sectional view of the eye during one embodied implant method utilizing ocular tissue surrounding a surgical incision to compress the deformable intraocular lens to an appropriate diameter with the aid of a first embodied microhook type instrument.

Referring now to FIGS. 31 and 32, there is illustrated a first embodied method comprising deforming the unique intraocular lens 30 by pushing a distal portion 30', of the lens 30 through a relatively small incision 15 made in the ocular tissue. A specially designed implantation instrument which may generally be described as a single microhook device comprising a very thin, relatively rigid shaft 51 having an engagement bend 52 in the forward portion thereof to engage the distal rim or hole of the intraocular lens 30 may be utilized to effect insertion of the lens through the incision 15. In this respect, the engagement bend 52 may be configured in a variety of ways, for instance, straight or outwardly curved bend, to facilitate engagement of the distal rim or hole in the intraocular lens 30.

Accordingly, the microhook device engaged with the lens 30 is initially inserted through the incision 15 and the lens 30 undergoes deformation to an appropriate diameter by compression of the lens caused by the pressure exerted by the surrounding tissue around the incision 15. The lens 30 is thereafter fully inserted into the eye in a desired position. Optionally, the microhook implantation instrument can be provided with an additional tine to prevent the rim of the lens from sliding over the needle, deleteriously releasing tension on the lens.

Figure 33:
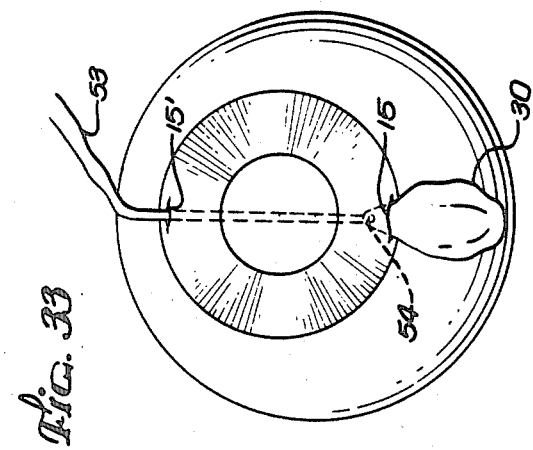
FIG. 33 is a front sectional view of the eye during a second embodied insertion technique of the intraocular lens and further illustrates the use of surgical connecting material removably attached to the periphery of the lens to pull the lens as it is deformed through the incision.
Figure 34:
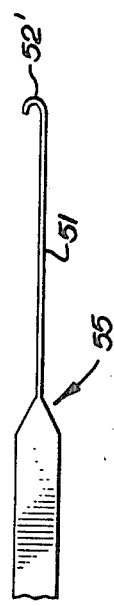
FIG. 34 is a side sectional view of a second embodied microhook type instrument which can be utilized in place of the surgical connecting material to assist pulling of the deformable intraocular lens through the incision and into the desired position in the eye.

A second embodied method is depicted in FIG. 33, the method also features the use of the surgical incision 15 to deform the intraocular lens 30. In this embodied form, the lens 30 is pulled through the surgical incision 15 by use of a connecting material 53, such as suture thread or the like. The connecting material 53 has been inserted through a second micro incision 15', on the opposite portion of the eye, and passed through a hole 54 provided in the periphery of the lens 30 and returned through the original incision 15. Accordingly, the two ends of the connecting material 53 are grasped and withdrawn which allows the lens 30 to be pulled into proper position into the eye. Once positioned inside the eye, one end of the connecting material 53 is released and the entire connecting material 53 is withdrawn, leaving the lens 30 in position. As shown in FIG. 34, a microhook type device 55 can be used in place of the connecting material 53 to pull the lens 30 into the eye from a second micro incision 15, made therein.

Figure 36:
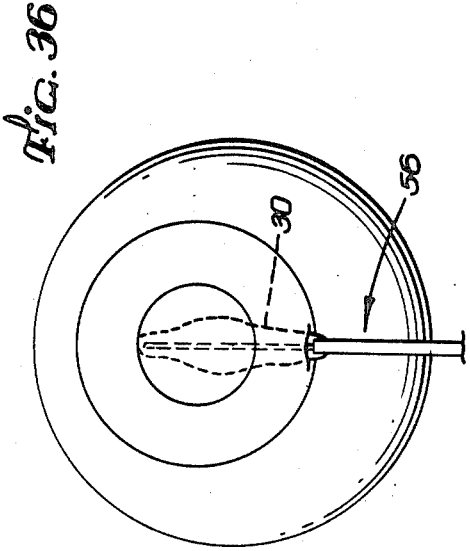
FIG. 36 is a front sectional view of the eye illustrating a third embodied implant procedure utilizing the double microhook type instrument shown in FIG. 35 to stretch the deformable intraocular lens during insertion of the lens into the desired position in the eye.
Figure 35:
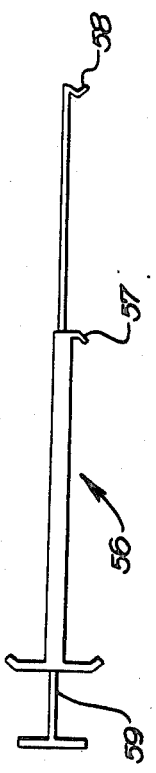
FIG. 35 is a side view of a third embodied microhook type instrument, including a double hook system designed to stretch the deformable intraocular lens in a direction perpendicular to the incision as an alternative procedure to the tissue stress technique shown in FIGS. 31 and 33.

Referring now to FIGS. 35 and 36, there is illustrated yet another embodied method for implantation of the lens 30 in the eye. In this embodied form, a double microhook type device 56 shown in FIG. 35 is utilized to stretch the intraocular lens 30 in a direction perpendicular to the incision 15, thereby deforming the lens 30 in the plane of the incision 15 sufficiently to allow insertion of the lens 30 through a relatively small incision 15, without ocular tissue stress as featured in the foregoing embodiments.

The double microhook device 56, as shown in FIG. 35, comprises parallel positioning of two needles 57 and 58, either co-axial or side-by-side, which facilitates one-handed operation by the surgeon. It should be understood however, that the same deformation can be accomplished in a bimanual operation with, for instance, the two microhook devices 50 and 55, shown in FIGS. 32 and 34.

In more detail, the device 56 depicted in FIG. 35 comprises a first needle 57 slideably mounted in association with a second needle 58 in such a manner as to be used as a means for retaining the lens 30 by engaging the proximal portion of the lens 30 to stabilize the lens 30 while the second needle 58 engages a distal portion of the lens 30. The force necessary to deform the lens 30 is applied by means of the plunger 59 so as to move the two hooks 57 and 58 away from each other, thereby stretching the engaged lens 30.

Referring now to FIGS. 37 through 46, there is illustrated yet another embodied method and inventive device 60 for implantation of the deformable intraocular lens 30 in accordance with the present invention.

More particularly, FIG. 37 depicts an implantation device 60 utilizing mechanical/hydraulic deforming force. The device 60 comprises a chamber 61 with an inlet opening 62 and a small outlet opening 63 designed for placement in or adjacent to a small incision 15. In this respect, the deforming force, either mechanical, hydraulic or pneumatic force, is applied through the inlet opening 62 of the device 60 in such a manner that the lens 30 is forced into and through the small outlet 63 and into the eye through the cannula 64 at the distal end of the device.

The intraocular lens 30 is initially positioned in the chamber 61 between the source of pressure, for instance, a manual syringe 65 as depicted, or other suitable system, and the orifice 66 through which it will pass before entering the eye. Optionally, the lens holding chamber 61 may be fabricated from a sterile transparent material so that the lens 30 may be inspected without opening the chamber 61 to avoid exposure of the contents to undesirable contamination. The device as shown in FIG. 41, may comprise a relatively short nozzle 67 to facilitate anterior or posterior chamber lens placement. Alternatively, the device may be fitted with a relatively long nozzle 68 to facilitate placement of the lens 30 through the pupil 12 into the posterior chamber 18.

FIG. 38 most clearly illustrates the lens holding chamber 61 of the device 60 shown in FIG. 37. The lens holding chamber 61 is preferably composed of transparent material and appropriately designed to contain the lens 30 in a natural, unstressed state. Preferably, the lens 30 before insertion and within the chamber 61, is suspended in a suitable liquid medium such as distilled water, saline or a biocompatible lubricating fluid such as hyaluronic acid or condroitin sulfate. As shown in FIG. 38, the chamber 61 in one embodied form is adapted to hold a lens 30 without supporting appendages and having a circular optical zone portion 31. However, it should be understood that such chamber can be adapted in a variety of configurations to facilitate placement of various intraocular lens structure in accordance with the present invention.

FIG. 39 depicts the lens 30 undergoing deformation by the action of fluid pressure as it is applied from the rear of the chamber 61 forcing the lens 30 into the narrow cannula 64 and outlet opening 63 which has been preplaced through the incision 15 made in the ocular tissue.

As shown in FIG. 40, the lens 30 returns to its natural, unstressed state as it exits from the relatively long nozzle 68 in the eye. In accordance with the present invention, the memory characteristics of the inventive lens are imparted by appropriate selection of lens material, and the combination of lens dimensions and fabrication techniques which imparts the desired lens configuration. The deformable optical zone portion of the lens must have an elongation to break of at least about 50 percent and preferably in the range of from about 50 percent to about 200 percent or higher.

FIG. 41 further illustrates positioning of the lens holding chamber 61 of the device 60 shown in FIG. 37 equipped with a short nozzle 67 for releasing the lens 30 just through the incision 15, as an anterior chamber or posterior chamber (through iridectomy or pars plana) placement.

FIG. 42 illustrates an alternative embodiment in which an extension cannula creating a long nozzle 68 is utilized to facilitate placement of the lens 30 in the posterior chamber 18 through the pupil 12.

FIGS. 43 through 46 are cross-sectional views of the lens 30 while deformed in the cannula 64 of the device 60. In this regard, FIG. 43 illustrates the lens 30 deformed in a rolled condition; FIG. 44 illustrates the lens 30 deformed in a folded condition, accordion style fold,; FIG. 45 illustrates a deformed lens 30 in a partly rolled and partly folded condition; and FIG. 46 illustrates a deformed lens 30 in a random "crumple" folded condition as might be anticipated in the implantation techniques shown in FIGS. 31 and 33.

FIG. 47 depicts yet another embodied implantation device 70 in accordance with the present invention of the "injection type". In this embodied form, the intraocular lens 30 is packaged in a lens holding compartment 71 as generally shown in FIG. 38, but the compartment 71 is adapted for mounting beyond the orifice 66 of the device 70. Accordingly, in this procedure, the deformable lens 30 is first removed from the compartment 71 and loaded into the cannula 72 of the device 70 shown in FIG. 47. The compartment 71 is thereafter detached, and the cannula 72 is inserted into the incision for placement of the lens 30 in the eye. The lens holding compartment 71, is therefore provided with a small outlet 73 designed for snug engagement with the nozzle 74 of the device 70 for placement in or adjacent to a small incision in the ocular tissue. The deformable lens is held in a substantially unstressed state until force, for instance, mechanical or suction, is applied through the outlet 73 in such a manner as to engage the lens 30 and draw it through the outlet 73 and into the engaged nozzle 74 from which it will be injected into the eye.

In more detail, FIG. 48 illustrates one method of removing the lens 30 from the lens holding compartment 71 utilizing suction from the cannula 72 and with or without corresponding positive pressure from the other side.

FIG. 49 shows an alternate method for loading the cannula 72 by utilizing a microhook or connecting material 53 to pull the lens into place in a manner similar to that shown in FIG. 34.

The device shown in FIG. 47 may comprise a vale, hole, or other inlet to facilitate the removal of the lens from the compartment 71 to the nozzle 74.

FIG. 50 depicts yet another implantation instrument 75 designed to simultaneously grasp and compress the deformable intraocular lens 30 to allow insertion of the lens 30 directly or indirectly into the eye. The embodied device 75 is of the forceps type and comprises a forward end 76 to encase the lens therein when closed. The forceps type device 75, may be modified as shown in FIG. 51 in which the ends 76', of the device are shortened and hollowed to compress the lens with a minimal amount of instrument material in the maximum cross-sectional volume present in the incision. Of course, other modifications to the device can be made such as the provision of holes, cut-outs and the like, to facilitate lens handling.

As shown in FIG. 52, the device 75 will partly deform the intraocular lens when the forceps are in a partially closed state. Two plates or sheets 77 and 78 over and under the lens may be included to facilitate encasing the lens 30 entirely within the ends 76.

FIG. 53 thus illustrates the forceps type device 75 with a lens completely encased therein.

FIG. 54 illustrates an alternate arrangement of the forceps ends 76" so that the ends 76" contact or hinge first at the top and then close at the bottom. A bowl-shaped compressing mechanism may optionally facilitate lens encasement for this embodied form which enhances lens release performance within the eye.

FIG. 55 illustrates in more detail the embodied device 75" of FIG. 54. In FIG. 55, the lens 30 is completely encased within the ends 76" of the device.

FIG. 56 further illustrates the surgical procedure for implantation of the lens 30 in the posterior chamber 18 through a relatively small incision 15 and iridectomy utilizing one embodied form of the forceps type device.

FIG. 57 depicts the use of a forceps type device 75 of the cut-away variety to place the lens 30 in the posterior chamber 18 through the pupil 12. It should be understood however, that these devices can readily position the lens 30 in the anterior chamber 17 as well.

FIGS. 58 and 59 depict yet another embodiment of the forceps type device. In this embodied form, the device 79 includes the use of hydraulic pressure to be applied for ejection of the lens 30 from the ends 76 and into the eye. In this respect, mechanical, hydraulic or pneumatic pressure may be exerted by a tube or pipe 80 mounted on an adjacent portion of the device 79.

As previously mentioned, the present invention is readily adapted to implant lens for refractive correction of the human crystalline lens without removal thereof. As shown in FIGS. 60 and 61, the intraocular lens 47 is placed in the posterior chamber 18 between the iris 11 and the human crystalline lens as shown in FIG. 60. The lens 47 illustrated is of the type shown in FIGS. 19 and 20 herein.

FIG. 61 shows an alternate positioning of the lens 47 shown in FIGS. 19 and 20 positioned in the anterior chamber 17 of the eye with the natural crystalline lens still intact and in place.

Typically, the inventive intraocular lens structure will have a total length of from about 9 millimeters to about 14 millimeters, a width of from about 4 millimeters to about 14 millimeters and can be fabricated having a wide range of index of refraction. The deformable optical zone portion will typically have a thickness of from about 0.1 millimeters to about 1.0 millimeters and a diameter in the range of from about 4 millimeters to about 6 millimeters.

Any conventional method for manufacture of the inventive lens can be utilized in accordance with the present invention to insure that the lens has an elongation to break within the prescribed range as aforementioned herein. For instance, compression molding, transfer molding, injection molding, casting, machining, or combination of these techniques may be utilized to produce the inventive lens.

The deformable intraocular lens structures in accordance with the present invention also facilitate removal of the lens from the eye atraumatically should a complication arise arise after implant, necessitating its removal from the eye.

Those skilled in the art will readily appreciate that other less preferred procedures could be utilized to effect deformation of the lens during implantation. For instance, a lens fabricated from hydrophilic material could be implanted in a dry state and hydrated once in position to return to its desired configuration and fixed focal length. Alternatively, the lens could be implanted in a plurality of separate components which are built up in the eye and suitably attached to one another, for instance by a medical grade adhesive.

The lens holding chamber and lens holding compartment of the implantation devices depicted in FIGS. 37 through 49 can, of course, be fabricated having a wide variety of suitable configurations for containing the deformable intraocular lens therein. In this respect, the chamber and compartment having pre-deformed lenses contained therein can be conveniently dispensed separately from the injection type devices.

Additionally, the intraocular lens structure in accordance with the present invention may comprise a base member having at least one surface layer thereon. For instance, a base member composed of an elastomer can be encased within a surface layer of hydrophilic material to enhance tissue compatability.

Accordingly, the present invention offers a unique implantation system for correction of or replacement of human crystalline lens after, for instance, cataract removal by way of small incision techniques. The system therefore provides an implantation technique with attendant surgical safety, convenience and a comfortable fit for the eye.

The described lens implant procedure and devices, thus minimize the principle disadvantages attendant with conventional rigid intraocular lens implantation which requires a relatively large incision in the ocular tissue which, among other disadvantages, leads to a relatively high complication rate and longer recovery times.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. A surgical device for implantation of an artificial intraocular lens in the eye through a relatively small incision made in the ocular tissue, said device comprising a chamber in a forward end of said device; means for containing said intraocular lens in an unstressed state and for orienting said intraocular lens in a prescribed orientation to facilitate anterior or posterior chamber lens placement substantially perpendicular to the optical axis, said lens having a deformable optical zone portion; means for exerting a force on said lens sufficient to deform said lens such that said optical zone portion is deformed to a diameter of 80% or less than the cross-sectional diameter of said optical zone portion in an unstressed state and to expel said lens from said device for placement of said lens in the eye.

2. The surgical device as defined in claim 1 wherein said force on said lens sufficient to deform said lens is a hydraulic deforming force.

3. The surgical device as defined in claim 1 wherein said force on said lens sufficient to deform said lens is a pneumatic deforming force.

4. The surgical device as defined in claim 1 wherein said force on said lens sufficient to deform said lens is mechanical deforming force.

5. The surgical device as defined in claim 1 wherein said means for containing said intraocular lens comprises a lens holding chamber having an inlet opening and an outlet opening and said force exerted on said lens is applied through said inlet opening to cause said lens to be expelled from said outlet opening and through a cannula intermediately disposed between said inlet opening and said outlet opening.

6. The surgical device as defined in claim 5 wherein said lens holding chamber is fabricated from a sterile, transparent material.

7. The surgical device as defined in claim 5 wherein said intraocular lens is pre-deformed and contained within said lens holding chamber.

8. The surgical device as defined in claim 5 and further comprising a relatively short nozzle disposed on the forward end of said cannula.

9. The surgical device as defined in claim 5 and further comprising a relatively long nozzle disposed at the forward end of said cannula.

10. The surgical device as defined in claim 1 wherein said means for exerting a force on said lens sufficient to deform said lens comprises a manual syringe.

11. The surgical device as defined in claim 5 wherein said lens holding chamber is detachable from said device.

12. The surgical device as defined in claim 11 wherein said lens holding chamber comprises an outlet adapted to snugly engage a nozzle of the device wherein said intraocular lens is transferred from said lens holding chamber to said cannula and said lens holding chamber is detached from said device, said nozzle is utilized for placement within said incision made in the ocular tissue.

* * * * *